| United States Patent [19] | [11] | 4,122,077 |
|---|---|---|
| Sarantakis | [45] | Oct. 24, 1978 |

[54] SOMATOSTATIN ANALOGS

[75] Inventor: Dimitrios Sarantakis, West Chester, Pa.

[73] Assignee: American Home Products Corporation, New York, N.Y.

[21] Appl. No.: 860,279

[22] Filed: Dec. 13, 1977

Related U.S. Application Data

[63] Continuation-in-part of Ser. No. 751,914, Dec. 17, 1976, abandoned, and a continuation-in-part of Ser. No. 751,915, Dec. 17, 1976, abandoned.

[51] Int. Cl.² .................... C07C 103/52; A61K 37/00
[52] U.S. Cl. .............................. 260/112.5 S; 424/177
[58] Field of Search .................. 260/112.5 S; 424/177

[56] References Cited

FOREIGN PATENT DOCUMENTS 839,405  10/1976  Belgium ............................ 260/112.5 S Primary Examiner—Delbert R. Phillips
Attorney, Agent, or Firm—Robert Wiser

[57] ABSTRACT

Somatostatin analogs which contain certain D-amino acid residues are disclosed. These analogs contain, in addition to a D-Trp$^8$ residue, glycyl or D-amino acid residues in positions 4 and 5.

These compounds inhibit the release of pituitary growth hormone, glucagon, and insulin.

7 Claims, No Drawings

SOMATOSTATIN ANALOGS

CROSS-REFERENCE TO COPENDING APPLICATIONS

This application is a continuation-in-part of copending applications, Ser. No. 751,914 and 751,915, both filed on Dec. 17, 1976 now abandoned.

BACKGROUND OF THE INVENTION

The cyclic somatotropin-release inhibiting factor (SRIF), known as somatostatin, has been shown [Brazeau et al., Science, 179, 77 (1973)] to have the following structure:

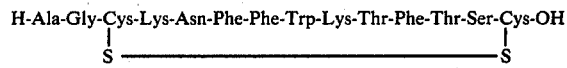

all amino acids being of the "natural" or L configuration.

Several methods for synthesizing somatostatin have been reported in the literature including the solid phase method of Rivier, J. Am. Chem. Soc., 96, 2986 (1974), and the solution methods of Sarantakis et al., Biochemical Biophysical Research Communications, 54, 234 (1973), and Immer et al., Helv. Chim. Acta, 57, 730 (1974); and there is much on-going peptide research whose goal is to enhance somatostatin's pharmacological activity by synthetically modifying its structure.

The present invention provides novel analogs of somatostatin wherein the Ala$^1$-Gly$^2$ residues may either be present or are replaced with H, Gly, Ala-Ala, or Gly-Gly-Gly; the L-Trp$^8$ residue is replaced with D-TrP$^8$; and the L-LYs$^4$-L-Asn$^5$ residues are replaced either with GLy or a residue derived from a specified D amino acid.

Replacement of the L-Trp residue in somatostatin by D-Trp$^8$ is discussed by J. Rivier et al., Biochem. Biophys. Res. Commun., 65, 746 (1975).

Somatostatin analogs wherein the L-Lys$^4$-L-Asn$^5$ residues are replaced with various amino acid residues are disclosed in Belgian Pat. No. 839,405.

SUMMARY OF THE INVENTION

The invention sought to be patented resides in the concept of a chemical compound selected from the class consisting of:

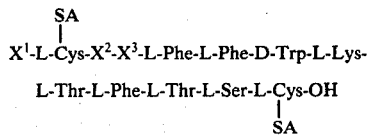

wherein A is hydrogen of the two A groups form a direct bond between the sulfur atoms; X$^1$ is H, Gly, L-Ala-Gly, L-Ala-L-Ala, or Gly-Gly-Gly; X$^2$ and X$^3$ may be the same or different and are chosen from Gly, D-Leu, D-Phe, D-Tyr, D-Trp, D-Met. D-His, D-Arg, D-Lys, D-Ser, D-Asp, or D-Asn, with the proviso that both may not simultaneously be Gly; and the pharmacologically acceptable addition salts thereof.

The tangible embodiments of the invention possess the inherent physical properties of being white to light than colored solids, are substantially insoluble in chloroform, benzene, and the like, but exhibit solubility in water and aqueous acid solution such as hydrochloric and acetic. The compositions of the invention display no clearly discernable melting points and may be purified by, for example, chromatographic means. Hydrolysis of the compositions of the invention in, for example, 4 N methanesulfonic acid allows determination of their amino acid content, which is consistent with the structures as hereinbefore set forth.

The tangible embodiments of the invention possess the applied use characteristic of inhibiting the release of the hormones somatotropin, glucagon, and insulin as evidenced by standard pharmacological test procedures.

The invention sought to be patented in its first subgeneric aspect resides in the concept of a chemical compound of the structure:

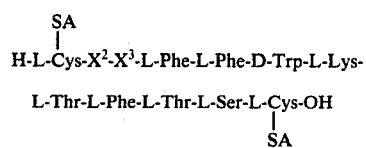

wherein A is hydrogen or the two A groups form a direct bond between the sulfur atoms; X$^2$ and X$^3$ may be the same or different and are chosen from Gly, D-Leu, D-Phe, D-Tyr, D-Trp, D-Met, D-His, D-Arg, D-Lys, D-Ser, D-Asp, or D-Asn, with the proviso that both may not simultaneously be Gly; and the pharmacologically acceptable addition salts thereof.

The invention sought to be patented in its second subgeneric aspect resides in the concept of a chemical compound of the structure:

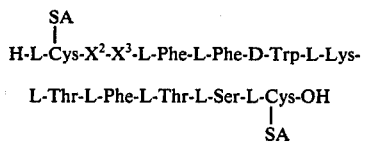

wherein A is hyrogen or the two A groups form a direct bond between the sulfur atoms; X$^2$ and X$^3$ may be the same or different and are chosen from D-Tyr, D-Trp, D-His, or D-Arg; and the pharmacologically acceptable addition salts thereof.

The invention sought to be patented in a specific aspect resides in the concept of the chemical compound which is:

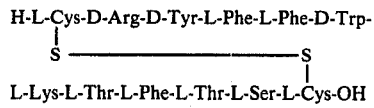

The invention sought to be patented in a second specific aspect resides in the concept of the chemical compound which is:

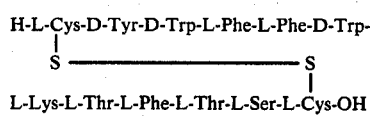

The invention sought to be patented in a third specific aspect resides in the concept of the chemical compound which is:

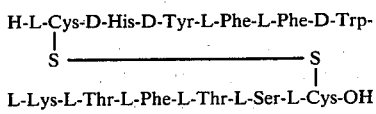

DESCRIPTION OF THE INVENTION

The polypeptide final products and their requisite intermediates are prepared by the well-known solid phase method as described by, for example, Merrifield, J. Am. Chem. Soc., 85, 2149 (1963). As applied to the compounds of this invention, α-amino and sulfhydryl protected cysteine is first attached to a chloromethylated polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group, the next desired protected amino acids are coupled individually to the resin supported sequence, seriatim. Alternatively, small peptide fragments may be prepared by, for example, the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is reported before the α-amino protecting group is removed for introduction of the next amino acid or amino acid sequence.

The preferred coupling reagents are 1-hydroxybenzotriazole and diisopropylcarbodiimide; other such reagents will be familiar to those skilled in the art.

After the desired amino acid sequence has been synthesized, the polypeptide is removed from the resin support by treatment with, for example, hydrogen fluoride and anisole to obtain the fully deprotected linear polypeptide. The cyclic disulfide may be produced by air oxidation.

Non-toxic addition salts of the linear and cyclic polypeptides are produced by methods well-known in the art from hydrochloric, hydrobromic, sulfuric, phosphoric, polyphosphoric, maleic, acetic, citric, benzoic, succinic, malonic, or ascorbic acid and the like. The acetic acid salt is preferred.

The protecting groups employed throughout the solid phase synthesis are well-known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thiourethane type protecting groups such as phenlthiocarbonyl; (6) alkyl type protecting groups as illustrated by triphenylmethyl (trityl); (7) trialkylsilane groups such as trimethylsilane. The preferred α-amino protecting group is tertbutyloxycarbonxyl. The side chain nitrogen atoms of arginine, denoted $N^{gn}$ are protected by a group which may be nitro,tosyl, benzyloxycarbonyl, adamantyloxycarbonyl or tert-butyloxycarbonyl, preferably the tosyl group.

Protection for the side chain amino group of lysine, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred. Protection for the hydroxyl group of threonine and serine may be with the acetyl, benzoyl, tert-butyl, benzyl. The benzyl group is preferred for this purpose.

The protecting group for the sulfhydryl group of the cysteinyl amino acid residue is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrogenzyl, etc.); trityl, benzyloxycarbonyl, benzhydryl, p-methoxybenzyloxycarbonyl, benzylthiomethyl, ethylcarbamoyl, thioethyl tetrahydropyranyl, acetamidomethyl, benzoyl, s-sulfonate salt, etc.; the p-methoxybenzyl group being preferred. The demonstrated pharmacological activity of the peptides of the invention characterizes the compounds as useful in the treatment of acromegaly and juvenile and adult-onset diabetes in the same manner as somatostatin itself. Administration of the peptides may be by conventional routes common to somatostatin and related polypeptides, under the guidance of a physician in an amount dictated by the extent of the dysfunction as determined by the physician. The compounds may be administered alone or in conjunction with conventional pharmaceutically acceptable carriers and adjuvants, in unit dosage form.

The following examples further illustrated the best mode contemplated by the inventor for the practice of the invention.

EXAMPLE 1

N-α-Tert-Butyloxycarbonyl-S-p-Methoxybenzyl-L-Cysteinyl-$N^{gn}$-Tosyl-D-Arginyl-O-2,6-Dichlorobenzyl-D-Tyrosyl-L-Phenylalanyl-L-Phenylalanyl-D-Tryptophyl-$N^{\epsilon}$-2-Chlorobenzyloxycarbonyl-L-Lysyl-O-Benzyl-L-Threonyl-L-Phenylalanyl-O-Benzyl-L-Threonyl-O-Benzyl-L-Seryl-S-p-Methoxybenzyl-L-Cysteinyl Hydroxymethyl Polystyrene Chloromethylated polystyrene resin (Lab System, Inc.) 1% cross-linked with divinylbenzene was esterified with Boc-Cys (SMBzl)-OH according to Gisin, Helv. Chim. Acta, 56, 1976 (1973). The polystyrene resin ester was treaed according to Schedule A for the incorporation of Boc-Ser(Bzl)-OH, Boc-Thr(Bzl)-OH, Boc-Phe-OH, Boc-Thr(Bzl)-OH, Boc-Lys(CIZ)-OH, Boc-D-Trp-OH, Boc-Phe-OH, Boc-Phe-OH, Boc-D-Tyr(Cl₂Bzl)-OH, Boc-D-Art(Tos)-OH and Boc-Cys(SMBzl)-OH to afford the title peptidoresin.

Schedule A

1. Wash with $CH_2Cl_2 \times 3$.

2. Treat with TFA-CH$_2$Cl$_2$-EDT (1:1:5%, v/v) for 5 minutes.
3. Treat as in 2 for 25 minutes.
4. Wash with CH$_2$Cl$_2$ × 3.
5. Wash with DMF.
6. Treat with 12% TEA in DMF × 2 for 3 minutes.
7. Wash with DMF.
8. Wash with CH$_2$Cl$_2$ × 3.
9. Treat with 4 equivalents of the corresponding amino acid derivative in CH$_2$Cl$_2$-DMF and stir for 5 minutes.
10. Add in two portions 5 equivalents of DIC dissolved in CH$_2$Cl$_2$ and over a period of 30 minutes. Reaction time 6 hours.
11. Wash with DMF × 3.
12. Wash with CH$_2$Cl$_2$ × 3.
13. Test ninhydrin reaction according to Kaiser et al., Annal. Biochem., 34, 595 (1970). In case of incomplete reaction, repeat lines 9 to 13 as above.

EXAMPLE 2

L-Cysteinyl-D-Arginyl-D-Tyrosyl-L-Phenylalanyl-L-Phenylalanyl-D-Tryptophyl-L-Lysyl-L-Threonyl-L-Phenylalanyl-L-Threonyl-L-Seryl-L-Cysteine (Cyclic 1-12) Disulfide (A)

The peptidoresin of the previous example (10.2 g.) was mixed with anisole (20 ml.) and treated with liquid HF (200 ml.) for 45 minutes in an ice-bath. The excess HF was removed in vacuo and the residue was extracted with 25% aqueous AcOH. The aqueous solution was extracted with ether and then the aqueous phase was neutralized with dilute NH$_4$OH to pH 7 and left to stand for 2 days in the open air. The mixture was acidified with glacial AcOH to pH 5 and lyophilyzed. The crude product was applied onto a column of Sephadex G-15 and eluted with 10% aqueous AcOH. Fractions of 5.5 ml. were collected and the material which emerged between fractions 96 to 126 was collected to yield 260 mg. of L-cysteinyl-D-arginyl-D-tyrosyl-L-phenylalanyl-L-phenylalanyl-D-tryptphyl-L-lysyl-L-threonyl-L-phenylalanyl-L-threonyl-L-seryl-L-cysteine (cyclic 1-12) disulfide as the diacetic acid salt.

R$_f$(BWA, 4:5:1 v/v) 0.52
R$_f$(BWAP, 30:24:6:20 v/v) 0.77
BWA = Butanol:Water:Acetic Acid
BWAP = Butanol:Water:Acetic Acid:Pyridine Amino Acid Analysis: Thr (2) 1.76, Ser (1) 0.88, Tyr (1) 0.95, Phe (3) 3, LYs (1) 1.09, Arg (1) 0.89, Trp and Cys N. D.

EXAMPLE 3

The in vivo pharmacological activity of the compound prepared in Example 2 (denoted compound A) was established by the following procedures with the indicated results:

SUPPRESSION OF GROWTH HORMONE

A subcutaneous (sc) injection of peptide solubilized or suspended in physiological saline, is given to Charles River CD ® nonfasted male rats. Matched saline control solution sc injected rats serve as control animals so that every experimental rat is paired with a control rat. The rats are kept in separate cages and 20 minutes before the end of the test time period they are given an intraperitoneal (i.p.) injection of Nembutal ® at a dose of 50 mg/kg. Blood samples are obtained by cardiac puncture and the plasma separated for the radioimmunoassay of growth hormone (GH) concentration (ng/ml.). Time periods after injection of 2, 4, 5, and 6 hours are generally used to test the duration of the activity of the peptide to suppress circulating peripheral GH levels. Comparisons between control and experimental GH values at each time are evaluated by the Student "t" test and statistical significance (p) at the 0.05 level or lower is used as the index of activity.

| Compound (Dose) | 2 Hr. | 4 Hr. | 5 Hr. | 6 Hr. |
| --- | --- | --- | --- | --- |
| Control | 171 ± 20 | 73 ± 21 | 60 ± 11 | 82 ± 21 |
| A (1 mg/kg.) | 17 ± 8 | 23 ± 8 | 32 ± 7 | 74 ± 14 |
|  | p = <0.001 | p = <0.05 | p = <0.05 | p = >0.05 |

SUPPRESSION OF GROWTH HORMONE, GLUCAGON AND INSULIN

Albino male rats are arranged in three groups (nine rats/group) and injected i.p. with nembutal at 50mg/kg. 15 minutes after the nembutal injection they are injected s.c. according to group with (a) test compound, typically 10–2000 μg/kg.; (b) SRIF 200 μg/kg.; or (c) physiological saline. 10 minutes later 0.5 ml. of arginine (300 mg/ml., pH 7.2) is injected into the heart. The rats are decapitated 5 minutes after receiving the arginine, and the blood is collected into Trasylol-EDTA. Appropriate aliquots are then assayed for growth hormone, glucagon and insulin. An active compound is one which significantly changes the plasma level of any of these hormones from that of the saline controls. Comparisons between control and experimental values are statistically evaluated by the analysis of variants method and statistical significance (p) at 0.05 or lower is used as the index of activity.

| Compound (Dose μg/kg.) | GH(ng/ml.) | Insulin (μU/ml.) | Glucagon (pg/ml.) |
| --- | --- | --- | --- |
| Control | 164 ± 38 | 213 ± 12 | 37 ± 8 |
| A (2000) | 20 ± 2 | 97 ± 18 | 8 ± 5 |
|  | p = <0.001 | p = <0.01 | p = <0.01 |
| Control | — | 221 ± 9 | 71 ± 6 |
| A (100) | — | 127 ± 20 | 24 ± 4 |
|  |  | p = <0.01 | p = <0.01 |
| Control | 163 ± 29 | 278 ± 32 | 69 ± 13 |
| A (10) | 11 ± 3 | 312 ± 52 | 39 ± 7 |
|  | p = <0.01 | p = >0.05 | p = <0.05 |

EXAMPLE 4

Tert-Butyloxycarbonyl-S-p-Methoxybenzyl-L-Cysteinyl-O-2,6-Dichlorobenzyl-D-Tyrosyl-D-Trytophyl-L-Phenylalanyl-L-Phenylalanyl-D-Tryptophyl-α-2-Chlorobenzyloxycarbonyl-L-Lysyl-O-Benzyl-L-Threonyl-L-Phenylalanyl-O-Benzyl-L-Threonyl-O-Benzyl-L-Seryl-S-p-Methoxybenzyl-L-Cysteinyl Hydroxymethylpolystyrene Chloromethylated polystyrene resin (Lab Systems Inc.) 1% cross-linked with divinylbenzene was esterified with BOC-Cys-(SMBzl)-OH according to Gisin, ibid. The polystyrene resin ester was treated according to Schedule A of Example 1 for the incorporation of BOC-ser(Bzl)OH, BOC-Thr(Bzl)OH, BOC-Phe-OH, BOC-Thr-(Bzl)OH, BOC-Lys(Clz)OH, BOC-D-Trp-OH, BOC-Phe-OH, BOC-Phe-OH, BOC-D-Trp-OH, BOC-D-Tyr(ClzBzl)OH and BOC-Cys(SMBzl)OH to afford the title peptidoresin.

EXAMPLE 5

L-Cysteinyl-D-Tyrosyl-D-Tryptophyl-L-Phenylalanyl-L-Phenylalanyl-D-Tryptophyl-L-Lysyl-L-Threonyl-L-Phenylalanyl-L-Threonyl-L-Seryl-L-Cysteine Cyclic (1-12)-Disulfide (B)

The peptidoresin of Example 4 (7.9 g.) was treated with liquid HF (150 ml.) in the presence of anisole (15 ml.) in vacuo and in an ice bath for 45 minutes. The excess HF was removed as fast as possible under vacuum (ca. 45 minutes) and the residue was taken in 25% aqueous AcOH. The polymeric support was filtered off and the filtrate was washed with ether then the aqueous phase was poured into 3.5 l. of deaerated water and the pH was brought to 7 with dilute $NH_4OH$. The disulfhydryl dodecapeptide was oxidized with $K_3Fe(CN)_6$ and then the pH was brought to 5 with glacial AcOH. The excess oxident was removed with ion exchange resin Bio Rad AG 3 and the peptide was absorbed on a Bio Rex 70 resin. Elution with pyridine buffer pH 7 afforded the crude dodecapeptide (300 mg.).

The crude material (150 mg.) was chromatographed through Sephadex G 15 (1.5 × 90 cm.) and eluted with 15% aqueous AcOH. The material which emerged in fractions (3.1 ml. each) 49 to 77 was pooled and lyophilyzed to yield L-cysteinyl-D-tyrosyl-D-tryptophyl-L-phenylalanyl-L-phenylalanyl-D-tryptophyl-L-lysyl-L-threonyl-L-phenylalanyl-L-threonyl-L-seryl-L-cysteine cyclic (1-12)-disulfide (69 mg.).

$R_f$(BWA, 4:1:1) 0.68
$R_f$(BWAP, 30:24:6:20) 0.86.
Amino Acid Analysis: Thr (2) 2.05, Ser (1) 1.05, Tyr (1) 0.96, Phe (3) 3, Lys (1) 1.04, Cys and Trp N. D.

EXAMPLE 6

The in vivo pharmacological activity of the compound prepared in Example 5 (denoted compound B) was established by the procedures set forth in Example 3 with the indicated results:

SUPPRESSION OF GROWTH HORMONE

| Compound (Dose) | Suppression of Growth Hormone | | | |
|---|---|---|---|---|
| | 2 Hr. | 2 Hr. | 4 Hr. | 5 Hr. |
| Control | 199 ± 27 | 303 ± 95 | 161 ± 30 | 158 ± 26 |
| B (1 mg/kg.) | 111 ± 14 | 133 ± 34 | 67 ± 14 | 151 ± 18 |
| | p = <0.01 | p = >0.05 | p = <0.01 | p = >0.05 |

| Suppression of Growth Hormone, Glucagon and Insulin | | | |
|---|---|---|---|
| Compound (Dose μg/kg.) | GH (ng/ml.) | Insulin (μU/ml.) | Glucagon (pg/ml.) |
| Control | 197 ± 26 | 166 ± 8 | 50 ± 5 |
| B (500) | 38 ± 6 | 116 ± 8 | 18 ± 4 |
| | p = <0.01 | p = <0.01 | p = <0.01 |
| Control | — | 171 ± 6 | 86 ± 6 |
| B (300) | — | 153 ± 9 | 38 ± 8 |
| | | p = >0.05 | p = <0.01 |
| Control | — | 278 ± 26 | 71 ± 9 |
| B (200) | — | 239 ± 17 | 44 ± 9 |
| | | p = >0.05 | p = <0.05 |
| Control | 171 ± 29 | 251 ± 50 | 32 ± 6 |
| B (100) | 43 ± 7 | 170 ± 15 | 5 ± 1 |
| | p = <0.01 | p = >0.05 | p = <0.01 |
| Control | 197 ± 26 | 166 ± 8 | 50 ± 5 |
| B (10) | 125 ± 26 | 162 ± 13 | 36 ± 4 |
| | p = >0.05 | p = >0.05 | p = <0.05 |

EXAMPLE 7

Tert-Butyloxycarbonyl-S-p-Methoxybenzyl-L-Cysteinyl-N-$^{im}$-Tosyl-D-Histidyl-O-2,6-Dichlorobenzyl-D-Tyrosyl-L-Phenylalanyl-L-PHenylalanyl-D-Tryptophyl-N$^\epsilon$-2-Chlorobenzyloxycarbonyl-L-Lysyl-O-Benzyl-L-Threonyl-L-Phenylalanyl-O-Benzyl-L-Threonyl-O-Benzyl-L-Seryl-S-p-Methoxybenzyl-L-Cysteinyl Hydroxymethyl Polystyrene Ester Chloromethylated polystyrene resin was esterified with BOC-Cys(SMBzl)OH according to Gisin, ibid., and the polymeric ester was treated according to Schedule A of Example 1 for the incorporation of BOC-Ser(Bzl)OH, BOC-Thr(Bzl)OH, BOC-Phe-OH, BOC-Thr(Bzl)OH, BOC-Lys(Clz), BOC-D-Trp-OH, BOC-Phe-OH, BOC-Phe-OH, BOC-D-Tyr(ClBzl)OH, BOC-D-His(Tos)OH, and BOC-Cys(SMBzl)OH, to afford the title peptidoresin.

EXAMPLE 8

L-Cysteinyl-D-Histidyl-D-Tyrosyl-L-Phenylalanyl-L-Phenylalanyl-D-Tryptophyl-L-Lysyl-L-Threonyl-L-Phenylalanyl-L-Threonyl-L-Seryl-L-Cysteine Cyclic (1-12)-Disulfide (C)

The peptidoresin of Example 7 (9.8 g.) was mixed with 18 ml. anisole and the mixture was treated with liquid HF in the absence of air and in an ice bath for 60 minutes, after which time the excess HF was removed under vacuo and the residue was extracted with 2M aqueous AcOH and filtered. The filtrate was poured into 7 liters of deaerated water and the pH was adjusted to 7.2 with $NH_4OH$. The mixture was stirred overnight (oxidation was complete) and then the pH was adjusted to 5 with gl. AcOH and the peptide was absorbed onto Amberlite CG-50 (H$^+$ form). The peptidic material was eluted with 30% aq. AcOH and lyophilized to yield 250 mg. of crude product.

The above material was chromatographed through a column of Sephadex G25 (2.5 × 57 cm.) and eluted with 10% aq. AcOH. The material which emerged in fractions (5.4 ml. each) 61-111 was pooled and lyophilized to yield the title dodecapeptide. TLC, Avicel precoated glass plates, chlorox-tolidine spray:

$R_f$(BWA, 4:11, v/v) 0.62
$R_f$(tet AmOH, P, W, 7:7:6, v/v) 0.80.
Amino Acid Analysis: Thr (2) 1.89, Ser (1) 0.91, Cys (2) 1.52, Tyr (1) 0.95, Phe (3) 3, Lys (1) 1.03, His (1) 0.93 Trp (1) 0.85. (tert AmOH, P, W = tertiary amyl alcohol, pyridine, water).

The following compounds were prepared in a fashion similar to that of the preceding examples:

EXAMPLE 9

L-Cysteinyl-D-Arginyl-D-Tryptophyl-L-Phenylalanyl-L-Phenylalanyl-D-Tryptophyl-L-Lysyl-L-Threonyl-L-Phenylalanyl-L-Threonyl-L-Seryl-L-Cysteine Cyclic (1-12)-Disulfide (D)

TLC, Avicel precoated glass plates, chlorox-todidine spray:

$R_f$(BWA, 4:1:1, v/v) 0.49
$R_f$(BWAP, 30:24:6:20, v/v) 0.77.
Amino Acid Analysis: Thr (2) 2.04, Ser (1) 1.09, Cys (2) 1.42, Phe (3) 3, Lys (1) 1.04, Trp (1) 0.77, Arg (1) 0.99.

EXAMPLE 10

L-Cysteinyl-D-Histidyl-D-Histidyl-L-Phenylalanyl-L-Phenylalanyl-D-Tryptophyl-L-Lysyl-L-Threonyl-L-Phenylalanyl-L-Threonyl-L-Seryl-L-Cysteine Cyclic (1-12)-Disulfide (E)

TLC, Avicel precoated glass plates, chlorox-tolidine spray:

$R_f$(BWA, 4:1:1, v/v) 0.43
$R_f$(BWAP, 30:24:6:20, v/v) 0.67.

Amino Acid Analysis: Thr (2) 1.93, Ser (1) 0.91, Cys (2) 1.53, Phe (3) 3, Lys (1) 1.06, His (2) 1.78.

EXAMPLE 11

L-Cysteinyl-D-Tryrosyl-D-Arginyl-L-Phenylalanyl-L-Phenylalanyl-D-Tryptophyl-L-Lysyl-L-Threonyl-L-Phenylalanyl-L-Threonyl-L-Seryl-D-Cysteine Cyclic (1-12)-Disulfide (F)

TLC, Avicel precoated glass plates, chlorox-tolidine spray:

$R_f$(BWA, 4:1:1, v/v) 0.55
$R_f$(tert AmOH, W, P, 7:6:7, v/v) 0.81.

Amino Acid Analysis: Thr (2) 1.91, Ser (1) 0.83, Cys (2) 1.45, Phe (3) 3, Tyr (1) 0.89, Lys (1) 1.02, Arg (1) 0.93, Trp (N.D.)

EXAMPLE 12

L-Cysteinyl-D-Leucyl-D-Tyrosyl-L-Phenylalanyl-L-Phenylalanyl-D-Trypotophyl-L-Lysyl-L-Threonyl-L-Phenylalanyl-L-Threonyl-L-Seryl-L-Cysteine Cyclic (1-12)-Disulfide (G)

TLC, Avicel precoated glass plates, chlorox-tolidine spray:

$R_f$(BWA, 4:1:1, v/v) 0.53
$R_f$(BWAP, 30:24:6:20, v/v) 0.85.

Amino Acid Analysis: Thr (2) 1.93, Ser (1) 0.86, Cys (2) 1.28, Leu (1) 0.95, Tyr (1) 0.91, Phe (3), Trp (N.D.)

EXAMPLE 13

L-Cysteinyl-D-Arginyl-D-Tyrosyl-L-Phenylalanyl-L-Phenylalanyl-D-Tryptophyl-L-Lysyl-L-Threonyl-L-Phenylalanyl-L-Threonyl-L-Seryl-D-Cysteine Cyclic (1-12)-Disulfide (H)

TLC, Avicel precoated glass plates, chlorox-tolidine spray:

$R_f$(BWA, 4:1:1, v/v) 0.48
$R_f$(BWAP, 30:24:6:20, v/v) 0.69.

Amino Acid Analysis: Thr (2) 1.79, Ser (1) 0.85, Phe (3) 3, Tyr (1) 0.95, Lys (1) 1.03, Trp (1) 0.69, Arg (1) 0.96, Cys (2) 1.22.

EXAMPLE 14

L-Cysteinyl-D-Tyrosyl-D-Tryptophyl-L-Phenylalanyl-L-Phenylalanyl-D-Tryptophyl-L-Lysyl-L-Threonyl-L-Phenylalanyl-L-Threonyl-L-Seryl-D-Cysteine Cyclic (1-12)-Disulfide (I)

TLC, Avicel precoated glass plates, chlorox-tolidine spray:

$R_f$(BWA, 4:1:1, v/v) 0.55
$R_f$(BWAP, 30:24:6:20, v/v) 0.87.

Amino Acid Analysis: Thr (2) 1.89, Ser (1) 0.86, Cys (2) 1.29, Tyr (1) 1, Phe (3) 3, Lys (1) 1.07, Trp (2) 0.93.

EXAMPLE 15

L-Cysteinyl-D-Tyrosyl-D-Glutamyl-L-Phenylalanyl-L-Phenylalanyl-D-Tryptophyl-L-Lysyl-L-Threonyl-L-Phenylalanyl-L-Threonyl-L-Seryl-L-Cysteine Cyclic (1- 12)-Disulfide (J)

TLC, Avicel precoated glass plates, chlorox-tolidine spray:

$R_f$(BWA, 4:1:1, v/v) 0.55
$R_f$(BWAP, 30:24:6:20, v/v) 0.69.

Amino Acid Analysis: Thr (2) 1.83, Ser (1) 0.82, Glu (1) 0.98, Cys (2) 1.33, Tyr (1) 0.95, Phe (3) 3, Lys (1) 1.01, Trp (1) 0.81.

EXAMPLE 16

The compounds of Examples 8 through 15 were assayed for suppression of growth hormone and for suppression of growth hormone, glucagon, and insulin, according to the procedures set forth in Example 3. The following results were obtained:

| Suppression of Growth Hormone | | | |
|---|---|---|---|
| Compound | Dose µg/kg. | Hours | GH ng/ml. |
| Control | — | 2 | 100 ± 16 |
| C | 1000 | 2 | 34 ± 1* |
| Control | — | 4 | 145 ± 35 |
| C | 1000 | 4 | 33 ± 2* |
| Control | — | 5 | 161 ± 28 |
| C | 1000 | 5 | 51 ± 8** |
| Control | — | 6 | 202 ± 39 |
| C | 1000 | 6 | 36 ± 3** |
| Control | — | 7 | 105 ± 13 |
| C | 1000 | 7 | 37 ± 5** |
| Control | — | 8 | 175 ± 52 |
| C | 1000 | 8 | 37 ± 6+ |
| Control | — | 2 | 302 ± 67 |
| D | 1000 | 2 | 28 ± 3** |
| Control | — | 4 | 177 ± 50 |
| D | 1000 | 4 | 11 ± 2* |
| Control | — | 2 | 93 ± 17 |
| E | 1000 | 2 | 36 ± 16 + |
| Control | — | 4 | 34 ± 11 |
| E | 1000 | 4 | 45 ± 10 |
| Control | — | 2 | 170 ± 23 |
| F | 1000 | 2 | 113 ± 34 |
| Control | — | 4 | 133 ± 25 |
| F | 1000 | 4 | 99 ± 11 |
| Control | — | 2 | 212 ± 37 |
| G | 1000 | 2 | 84 ± 11* |
| Control | — | 4 | 173 ± 25 |
| G | 1000 | 4 | 94 ± 23+ |
| Control | — | 5 | 243 ± 44 |
| G | 1000 | 5 | 93 ± 30 |
| Control | — | 6 | 109 ± 61 |
| G | 1000 | 6 | 72 ± 68 |
| Control | — | 2 | 191 ± 18 |
| H | 1000 | 2 | 75 ± 4** |
| Control | — | 4 | 169 ± 32 |
| H | 1000 | 4 | 144 ± 21 |
| Control | — | 2 | 187 ± 28 |
| I | 1000 | 2 | 49 ± 5** |
| Control | — | 4 | 148 ± 23 |
| I | 1000 | 4 | 86 ± 11+ |
| Control | — | 2 | 392 ± 59 |
| J | 1000 | 2 | 311 ± 68 |
| Control | — | 4 | 185 ± 27 |
| J | 1000 | 4 | 179 ± 39 |

*p <0.01;
**p <0.001;
+p <0.05

| Suppression of Growth Hormone, Glucagon and Insulin | | | |
|---|---|---|---|
| Compound | Dose µg/kg. | GH µg/ml. | INS µU/ml. | GLUN pg/ml. |
| Control | — | 268 ± 46 | 323 ± 28 | 379 ± 109 |
| C | 200 | 76 ± 14* | 254 ± 31 | 84 ± 25+ |
| Control | — | 365 ± 31 | 379 ± 47 | 336 ± 51 |
| C | 200 | 109 ± 10* | 273 ± 36 | 184 ± 22+ |
| C | 10 | 149 ± 23* | 252 ± 41 | 165 ± 13* |
| Control | — | 122 ± 26 | 195 ± 18 | 99 ± 22 |

| Suppression of Growth Hormone, Glucagon and Insulin | | | | |
|---|---|---|---|---|
| Compound | Dose µg/kg. | GH µg/ml. | INS µU/ml. | GLUN pg/ml. |
| D | 100 | 21 ± 2* | 35 ± 2* | 53 ± 9 |
| Control | — | 190 ± 28 | 295 ± 38 | 93 ± 12 |
| E | 200 | 34 ± 3* | 182 ± 18+ | 29 ± 12* |
| Control | — | 109 ± 21 | 226 ± 29 | 40 ± 4 |
| F | 100 | 11 ± 3* | 103 ± 24* | 24 ± 5+ |
| G | 100 | 29 ± 16+ | 218 ± 44 | 28 ± 16 |
| Control | — | 171 ± 29 | 224 ± 20 | 74 ± 4 |
| H | 25 | 23 ± 4* | 128 ± 11* | 56 ± 6+ |
| Control | — | 279 ± 53 | 323 ± 30 | 42 ± 6 |
| I | 200 | 57 ± 14* | 236 ± 27+ | 13 ± 2* |
| Control | — | 240 ± 34 | 211 ± 26 | 42 ± 7 |
| J | 100 | 128 ± 24+ | 263 ± 28 | 45 ± 4 |

*p <0.01;
+p <0.05

The subject matter which the Applicant regards as his invention is particularly pointed out and distinctly claimed as follows:

I claim:

1. A chemical compound of the structure:

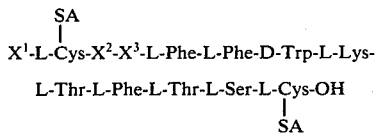

wherein A is hydrogen or the two A groups form a direct bond between the sulfur atoms; $X^1$ is H, Gly, L-Ala-Gly, L-Ala-L-Ala, or Gly-Gly-Gly; $X^2$ and $X^3$ may be the same or different and are chosen from Gly, D-Leu, D-Phe, D-Tyr, D-Trp, D-Met, D-His, D-Arg, D-Lys, D-Ser, D-Asp, or D-Asn, with the proviso that both may not simultaneously be Gly; and the pharmacologically acceptable addition salts thereof.

2. The chemical compounds of claim 1 wherein $X^1$ is hydrogen.

3. The chemical compounds of claim 1 wherein $X^2$ and $X^3$ are chosen from D-Arg, D-His, D-Trp, and D-Tyr.

4. The chemical compounds of claim 2 wherein $X^2$ and $X^3$ are chosen from D-Arg, D-His, D-Trp, and D-Tyr.

5. The chemical compound of claim 1 which is:

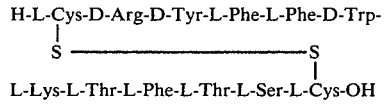

6. The chemical compound of claim 1 which is:

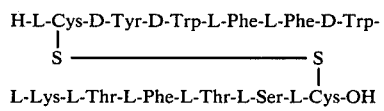

7. The chemical compound of claim 1 which is:

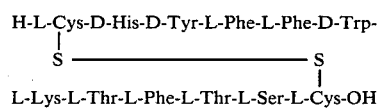

* * * * *